(12) United States Patent
Flock et al.

(10) Patent No.: US 7,889,339 B1
(45) Date of Patent: *Feb. 15, 2011

(54) COMPLEMENTARY WAVEPLATE ROTATING COMPENSATOR ELLIPSOMETER

(75) Inventors: Klaus Flock, Mountain View, CA (US); Jeff T. Fanton, Los Altos, CA (US)

(73) Assignee: KLA-Tencor Corporation, San Jose, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 12/170,367

(22) Filed: Jul. 9, 2008

Related U.S. Application Data

(60) Provisional application No. 61/034,049, filed on Mar. 5, 2008, provisional application No. 61/034,112, filed on Mar. 5, 2008.

(51) Int. Cl.
*G01J 4/00* (2006.01)

(52) U.S. Cl. ........................ 356/369; 356/364; 356/365; 356/366; 356/367; 356/368

(58) Field of Classification Search ......... 356/364–370; 250/225
See application file for complete search history.

(56) References Cited

U.S. PATENT DOCUMENTS

| | | | |
|---|---|---|---|
| 5,798,837 A * | 8/1998 | Aspnes et al. | 356/369 |
| 5,872,630 A * | 2/1999 | Johs et al. | 356/369 |
| 5,877,859 A * | 3/1999 | Aspnes et al. | 356/364 |
| 5,910,842 A | 6/1999 | Piwonka-Corle et al. | |
| 5,973,787 A | 10/1999 | Aspnes et al. | |
| 6,373,614 B1 | 4/2002 | Miller | |
| 6,417,892 B1 * | 7/2002 | Sharp et al. | 348/742 |
| 6,449,043 B2 | 9/2002 | Aspnes et al. | |
| 6,515,744 B2 * | 2/2003 | Wei | 356/369 |
| 6,822,738 B1 * | 11/2004 | Johs et al. | 356/369 |
| 6,882,421 B2 * | 4/2005 | Opsal et al. | 356/369 |
| 7,173,700 B2 | 2/2007 | Aspnes | |
| 7,349,079 B2 * | 3/2008 | Zhao et al. | 356/128 |
| 7,420,675 B2 * | 9/2008 | Giakos | 356/364 |
| 7,428,050 B2 * | 9/2008 | Giakos | 356/369 |
| 7,499,175 B1 * | 3/2009 | Palmer et al. | 356/450 |
| 7,701,561 B2 * | 4/2010 | Zou et al. | 356/73 |

OTHER PUBLICATIONS

Office Action dated Jun. 22, 2010 for U.S. Appl. No. 12/170,371.
U.S. Appl. No. 61/034,112, entitled "Normal Incidence Ellipsometer With Complementary Waveplate Rotating Compensators", filed Mar. 5, 2008.
U.S. Appl. No. 61/034,049, entitled "Complementary Waveplate Dual Rotating Compensator Ellipsometer", filed Mar. 5, 2008.

(Continued)

*Primary Examiner*—Sang Nguyen
(74) *Attorney, Agent, or Firm*—Joshua D. Isenberg; JDI Patent

(57) ABSTRACT

Ellipsometry using two waveplates of complementary retardation in a dual rotating compensator configuration is disclosed. Two waveplates of complementary retardation may be used to increase the useful spectral range of a rotating compensator ellipsometer, in particular towards the deep Ultraviolet (UV) spectrum. The improved rotating compensating ellipsometer disclosed herein enables a user to select specific and different waveplate retardations for the purpose of increasing the operating wavelength range of the rotating compensating ellipsometer.

50 Claims, 4 Drawing Sheets

OTHER PUBLICATIONS

U.S. Appl. No. 12/170,371, entitled "Normal Incidence Ellipsometer With Complementary Waveplate Rotating Compensators", filed Jul. 9, 2008.

Notice of Allowance and Fees Due dated Sep. 29, 2010 for U.S. Appl. No. 12/170,371.

* cited by examiner

COMPLEMENTARY WAVEPLATE ROTATING COMPENSATOR ELLIPSOMETER

CLAIM OF PRIORITY

This application claims the benefit of priority of commonly-assigned co-pending U.S. Patent Application No. 61/034,049, entitled "COMPLEMENTARY WAVEPLATE DUAL ROTATING COMPENSATOR ELLIPSOMETER", filed Mar. 5, 2008, the entire contents of which are incorporated herein by reference.

This application claims the benefit of priority of commonly-assigned co-pending U.S. Patent Application No. 61/034,112, entitled "NORMAL INCIDENCE ELLIPSOMETER WITH COMPLEMENTARY WAVEPLATE ROTATING COMPENSATORS", filed Mar. 5, 2008, the entire contents of which are incorporated herein by reference.

CROSS-REFERENCE TO RELATED APPLICATION

This application is related to commonly-assigned co-pending U.S. patent application Ser. No. 12/170,371, entitled "NORMAL INCIDENCE ELLIPSOMETER WITH COMPLEMENTARY WAVEPLATE ROTATING COMPENSATORS", which is filed the same date as the present application, the entire contents of which are incorporated herein by reference.

FIELD OF THE INVENTION

This invention generally relates to the field of ellipsometry and to the instrumentation associated with that field, namely ellipsometers and more particularly to rotating compensator ellipsometers.

BACKGROUND OF THE INVENTION

Ellipsometry is a technique that is being used to determine the polarization state of light. It is widely applied to accurately and precisely quantify changes in polarization of a probe beam after interaction with a sample. The measurement is contact free and generally non-destructive. The rate at which measurements can be performed depends, in principle, only on the speed of the data acquisition hardware, such as optical detectors, and on the light budget for the application. This makes ellipsometry not only accurate and precise but also inherently fast as well as relatively inexpensive. The available advantages of cost, precision, and accuracy allow ellipsometric techniques to be used for non-destructive high volume applications that would otherwise be too expensive, too time consuming, in-accurate, or in general be complex and non-trivial to realize.

An important example for the successful application of ellipsometry can be found in the semiconductor industry, where it is being used to measure the success rate (yield) of material deposition processes as well as micro-lithographic patterning processes for computer chip and memory production.

Ellipsometric measurements can be done in transmission or reflection, however, for applications that are specifically targeted at surface processes reflection measurements are more sensitive. In a typical configuration, an incident beam of light is polarized to contain only photons of a certain, known state of polarization. After reflection by the sample—which usually occurs at non-normal incidence and, for best sensitivity, close to Brewster's angle—the polarization of the probe beam has changed to be of some new and unknown state, which is generally an elliptical mode. Linear and circular modes are two special cases of elliptical modes. The polarization of the reflected beam is then measured by the detection arm of the instrument and the difference between detected polarization of the reflected beam and known polarization of the incident beam is being computed. The difference in polarization is attributed to the cumulative effect of the optical properties of the sample, which depends on the presence and thickness of one or multiple overlayers and the effective refractive index and absorption coefficient of overlayer and bulk material(s). Other sample properties to which ellipsometry is sensitive are (1) structural dimensions within surface and bulk material, where it is used for instance to measure the spacing of periodic ridges in so called critical dimensions analysis, (2) alloy composition, (3) crystallinity, etc. With models and assumptions that are suitable for the specimen, the desired structural and material properties may be inferred and quantified from the difference signal. The derived quantities are then compared to target values for process control purposes, or they may be analyzed for their fundamental physical significance for instance for material research and development purposes.

A typical example of an ellipsometer of the common rotating polarizer type is shown in FIG. 1. Light from a source 100 is polarized via polarizer 110 and is incident on the sample 120. The sample may include one or more overlayers 122. Rotation of the polarizer causes the polarization state to rotate as a function of time, which means that the magnitude of incident p- and s-polarized light is being modulated as the polarizer turns. The modulation of the incident light occurs at twice the polarizer rotation rate, since the polarizer has a 2-fold symmetry, i.e., azimuth angles of 0° and 180° result in the same transmitted intensity. The modified polarization state of the reflected beam is being projected onto the transmission axis of an analyzer 130, and the intensity that is transmitted by the analyzer is measured with a detector 140 as a function of polarizer azimuth. The Fourier Transform of the detected signal (harmonic analysis) yields two non-zero frequency components, of which the amplitude and the relative phase contain the information that we seek. Even though the same information can be obtained with so called NULL-ellipsometry, where the polarizer is not spinning, the type of modulation measurement described here has found widespread acceptance due to its simplicity and because it is better suited for continuous, fast operation than NULL-ellipsometry.

By denoting the reflective properties of the sample as $r_p$ and $r_s$ for light that is polarized parallel and perpendicular to the plane of incidence, respectively, the physical quantities that lend themselves to optical far field detection are (1) $|r_p|^2+|r_s|^2$ which is the normalized reflected intensity, (2) $|r_p|^2-|r_s|^2$ which is the difference between p- and s-polarized intensity, and (3) the phase shift $\Delta$ between p- and s-polarized constituents of the beam, which was introduced upon reflection by the sample. The term far-field refers to the region that is many wavelengths away from the source of the radiation, in this case the sample surface. Since optical wavelengths are small, on the order of nanometers, virtually all common optical applications involve only far-field detection. Without resorting to interferometric techniques, the most information that is available from such a measurement is the intensity for two orthogonal polarizations and the relative phase-shift between them.

The rotating polarizer system described above returns the intensity (1), the intensity excess of one polarization over the other (2), and (3) the cosine of the phase shift between p- and s-polarized light, i.e. cos(Δ). Not readily accessible are incident intensity and an overall phase. Equivalent information is obtained from a rotating analyzer system, where the polarizer is fixed and the analyzer rotates. It can be shown that the system is symmetric under time reversal, i.e. the direction of propagation does not matter in principle, except that source and detector are reversed. However, it is important to emphasize that both, rotating polarizer and rotating analyzer ellipsometers (RPE/RAE) can only return cos(Δ) and not Δ itself, which has significant yet not necessarily obvious implications for the application.

Whenever the relative phase shift between $r_p$ and $r_s$ happens to be in the vicinity of 0, π, 2π, etc. cos(Δ) assumes an extremum and hence is independent of a variation in Δ, which renders the system insensitive to small changes, for instance in overlayer thickness. This is a particular disadvantage for measuring very thin films, or whenever the thickness of an overlayer meets a resonance condition, i.e. for which the phase shift between p- and s-waves is an integer multiple of π. In these situations, all data is lost. In addition, the cosine is a symmetric function around Δ=0 and hence rectifies the phase shift, so that it is not possible to tell the handedness of the reflected elliptical mode.

The weakness of RPE/RAEs is resolved by introducing a rotating waveplate as shown in FIG. 2. Such a system is called a rotating compensator ellipsometer (RCE) and features a spinning quarter-waveplate 230, also sometimes called a compensator, while keeping polarizer and analyzer stationary. The quarter waveplate 230 is constructed out of a birefringent material, such as $MgF_2$, and is made of specific thickness to retard orthogonal polarization directions by 90°, i.e., a quarter of a wavelength. Modulation of the beam is introduced by rotating the direction of the 90° phase shift, hence the spinning waveplate. The intensity is measured in much the same way as in the RPE system, except that it is now a function of waveplate azimuth. The detector readout must be synchronized to the rotation of the compensator instead of the polarizer.

An RCE returns both cosine and sine of the relative phase Δ, which is equivalent to Δ itself, and therefore the sensitivity of the measurement does not depend on sample properties as in an RPE or RAE system. Whenever the cosine assumes a maximum, sine goes through zero, which means that sensitivity lost in one coefficient is re-distributed to the other coefficient, respectively, maintaining the overall information content of the signal. Hence an RCE is also called a complete system, since it returns all of the available optical information, while RPE/RAEs are considered incomplete systems. RPE/RAEs have proven to be simple and useful in the past, however, RCEs are being regarded as the more modern and more desirable systems due to the enhancement in diagnostic power, and their robustness and high precision that derives from stationary polarizer and analyzer prisms.

A new dimension is added to ellipsometry when measurements are done over a spectrum of wavelengths instead of a single wavelength, such as produced by a broadband light source, e.g. a Xenon arc lamp. All wavelengths are transmitted simultaneously through the system in a "white" beam and the different wavelength constituents are separated in space after the analyzer by means of a dispersive element, such as a grating or a prism, and detected for instance with an array detector such as a charge-coupled device (CCD) or a linear photo diode array (PDA). Such a broadband system, called a spectroscopic ellipsometer, offers the advantage of providing sample properties like the dielectric function of a material as a function of wavelength or, equivalently, energy. Further, spectroscopic ellipsometry is essential for samples with stratified single or multiple overlayers, which are encountered regularly in the manufacturing process of computer chips and memory devices. The penetration depth of light depends on the wavelength, so that the short wavelength part of the spectrum can be used to measure overlayer dielectric function as if it was bulk material, while the longer wavelengths penetrate deeper to reach the underlying interface, and together with knowledge of the dielectric function of the overlayer material provide the layer thickness. With thickness and dielectric function, the layer on top of the substrate can be characterized comprehensively.

Broadband operation is essential for many applications, however, rotating compensator systems are not ideally suited for it. The difficulty encountered with RCE operation is a consequence of the fact that the retardation of the waveplate depends on the wavelength of light approximately as $1/\lambda$, $\lambda$ being the wavelength, yet the retardation needs to be that of a quarter wave over the entire spectral range for best sensitivity. The retardation is more generally given by $\Delta n(\lambda) t / \lambda$, with $\Delta n$ being a difference in refractive index for the two orthogonal directions of the birefringent material and t being an effective thickness of the waveplate. For the sake of argument, a weak dependence of $\Delta n$ on wavelength may be assumed.

With the retardation increasing towards the short wavelength end of the spectrum, the sensitivity of the RCE gradually decreases and is reduced to that of an equivalent rotating polarizer system when it approaches 180°. Reducing the wavelength further, the sensitivity initially increases, assumes a second maximum at 270° but then hits a dead zone around 360° retardation, for which an RCE returns no phase information at all but becomes a simple off-axis reflectometer, which is even less useful than an RPE. Rotating polarizer systems on the other hand do not suffer from a wavelength dependence of sensitivity in that sense, since they are constructed out of essentially dispersion free components and need not contain a waveplate at all.

An example of a rotating compensator ellipsometer is described in U.S. Pat. No. 5,973,787, entitled "Broadband Spectroscopic Rotating Compensator Ellipsometer," granted to David E. Apnes of Apex, N.C. and Jon Opsal of Livermore, Calif. and assigned to Therma-Wave Corporation of Fremont, Calif., which discloses how a single-rotating-compensator system can be designed to cover a relatively wide range of retardation values, even though it does not have optimal sensitivity over the entire wavelength range and is limited in bandwidth. Extension of the available bandwidth into the extreme UV below 190 nm while retaining the visible to IR sensitivity is impossible with the prescribed broadband ellipsometer and the presently available waveplates.

One could, in principle, circumvent the wavelength restrictions of a rotating-compensator system by constructing it with an achromatic compensator, such as a Fresnel rhomb. However, these devices are non-trivial and expensive to manufacture, they are significantly bigger and heavier than a standard waveplate, and they feature unevenly distributed moments about the optical axis. Hence achromatic retarders are more difficult to use in a continuously, fast-rotating configuration than standard waveplates. Another practical requirement is that the exit beam be co-linear to the entrance beam, which is also non-trivial in the case of thick components, such as an achromatic retarder.

In summary, current single rotating compensator designs employ a waveplate that works reasonably well over a wide spectral range, yet, due to the dispersive nature of the material out of which the waveplate is constructed (typically $MgF_2$), the sensitivity is compromised at either the extremely short- or long wavelengths, or at both extremes. Specifically, 100% loss of the signal occurs at wavelengths where the retardation either approaches 0° or 360°, and partial loss of information occurs in the vicinity of 180° retardation.

Thus there is a need in the art of spectroscopic ellipsometry to overcome the bandwidth limitations of rotating compensator systems without reintroducing the well known shortfalls of rotating polarizer ellipsometers. One would like to have a complete system, such as an RCE, to detect all available optical information over the available wavelength range with optimal sensitivity. Such a system is proposed in this application.

BRIEF DESCRIPTION OF THE DRAWINGS

Other objects and advantages of the invention will become apparent upon reading the following detailed description and upon reference to the accompanying drawings in which.

DESCRIPTION OF THE SPECIFIC EMBODIMENTS

Although the following description contains many specific details for the purposes of illustration, anyone of ordinary skill in the art will appreciate that variations and alterations are within the scope of the invention. Accordingly, the exemplary embodiments of the invention described below are set forth without any loss of generality to, and without imposing limitations upon, the claimed invention.

In the embodiments of the present invention a second waveplate is added to a single rotating compensator ellipsometer. The second waveplate provides a quarter wavelength retardation that is at least partly different and complementary to that of the first waveplate in order to increase the spectral range for which useful retardation is available, especially toward the short wavelength end of the available spectrum. The sensitivity of the system may also be increased in the conventional spectral range, since each of the two waveplates may be optimized for its own, more narrow spectral range of operation. With the proper choice of two waveplates of different retardation, the useful spectral range can be extended, e.g., from typically 190-850 nm to 150-1000 nm, and beyond if necessary, while increasing the sensitivity within the conventional wavelength range at the same time.

Figure 3:
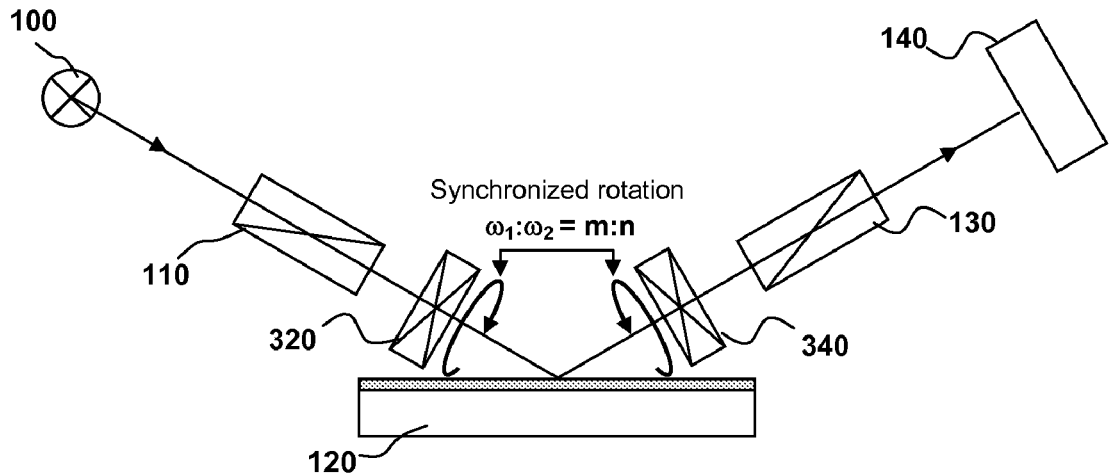
FIG. 3 is a schematic diagram of a prior art dual rotating compensator ellipsometer with two identical waveplates.

Even though the idea of using a dual rotating compensator ellipsometer configuration is not novel in principle, prior implementations were designed either to eliminate systematic artifacts by providing additional information about the optical configuration, such as a phase shift introduced by focusing optics that would distort the sample information if it were unaccounted, or they were designed to extract additional information about the sample, as it is the case in the so called Mueller matrix spectroscopy. These applications are special cases which can provide valuable information in certain circumstances, but which do not constitute the majority of use cases for spectroscopic ellipsometry at the present time. In particular, in the prior art systems the second waveplate must generally be optimized for the same wavelength or wavelength range as the first waveplate and must hence be identical or nearly identical in the effective (optical) thickness to the first waveplate if both waveplates are constructed out of the same material. More generally, the retardation of both waveplates must be about the same in order to provide with sufficient sensitivity the additional information sought with these systems. Also, many prior art systems were designed primarily for use with narrow-band sources, e.g. lasers, and are specifically not targeted to increase the wavelength range of operation. A schematic diagram of a dual rotating compensator system with identical or nearly identical waveplates depicting the prior art is provided in FIG. 3. These systems were typically constructed in a configuration where the two waveplates 320 and 340 are located (symmetrically) on either side of the sample 120.

Figure 4:
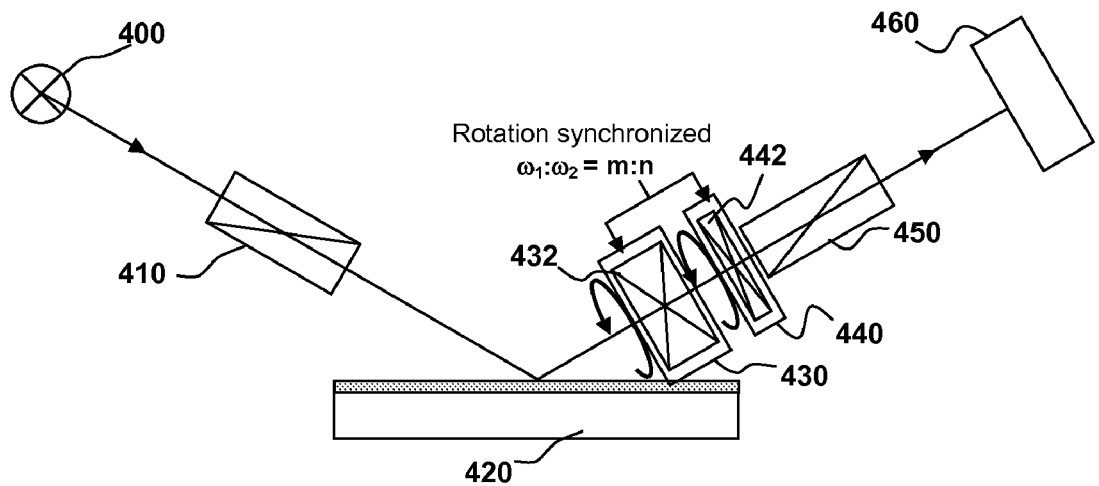
FIG. 4 is a schematic diagram of a complementary dual rotating compensator ellipsometer according to the first embodiment of the present invention; it features two waveplates of specific and different thickness mounted on the same side of the sample in the so called single waveplate equivalent configuration.

In contrast, FIG. 4 shows the first embodiment of the novel complementary dual rotating compensator ellipsometer disclosed herein. It enables the user to select specifically two waveplates 430 and 440 of different thickness so that their respective quarter wave retardation occurs at different wavelengths. The sole purpose of this configuration is to increase the wavelength range of useful sensitivity and to optimize the sensitivity over all available wavelengths.

Figure 1:
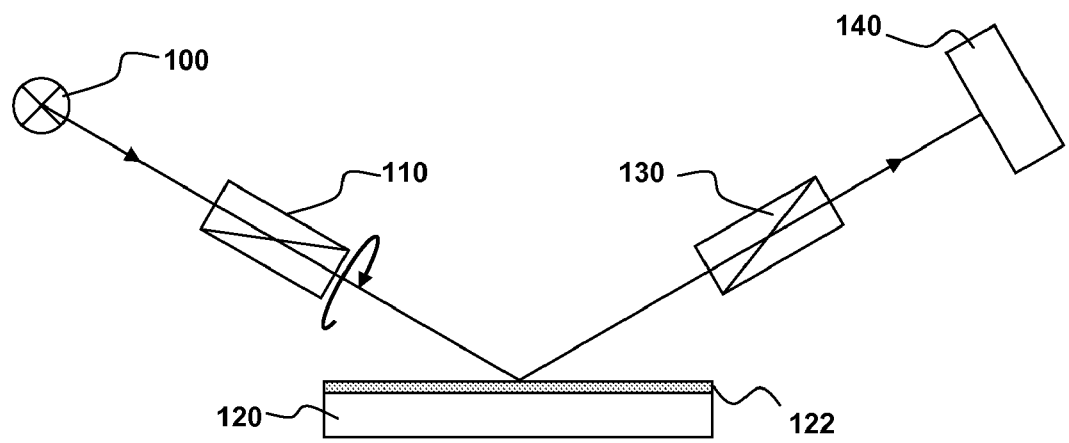
FIG. 1 is a schematic diagram of a prior art rotating polarizer ellipsometer.
Figure 2:
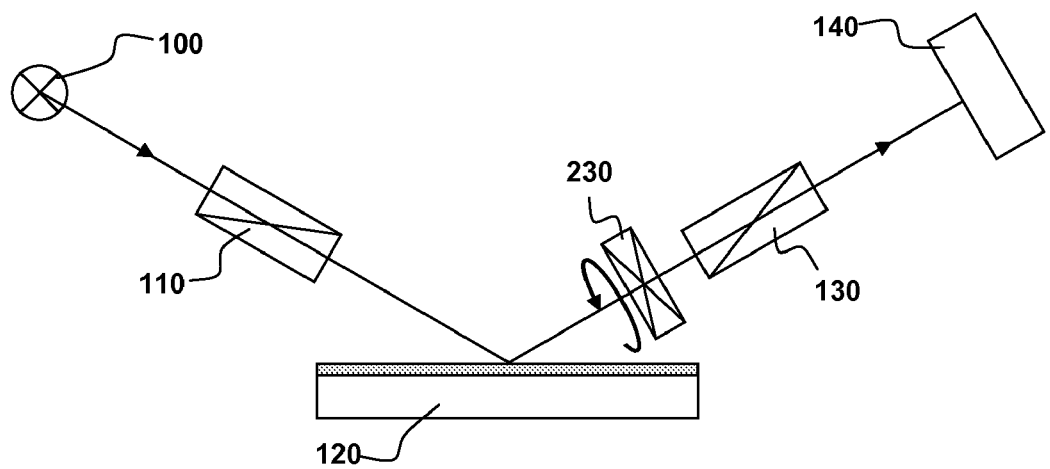
FIG. 2 is a schematic diagram of a prior art rotating compensator ellipsometer.

In the embodiment illustrated in FIG. 4, referred to herein as the single waveplate equivalent configuration, both waveplates are located next to each other on the same side of the sample. In the (idealized) case of truly complementary waveplates, this configuration returns the same information as a single rotating compensator system, since the incident light has the same polarization state as in the RCE configuration of FIG. 2, yet the useful wavelength range for the system is much extended. Specifically, the second waveplate does not modulate the incident light as in the traditional symmetric dual compensator configuration of FIG. 3, and that is desirable for the majority of applications, where the additional sensitivity is neither significant nor wanted but would add to the complexity of data analysis. This configuration is specifically not targeted at either Mueller matrix spectroscopy or to extract information about the measurement hardware in addition to that of a single rotating compensator system.

Figure 5:
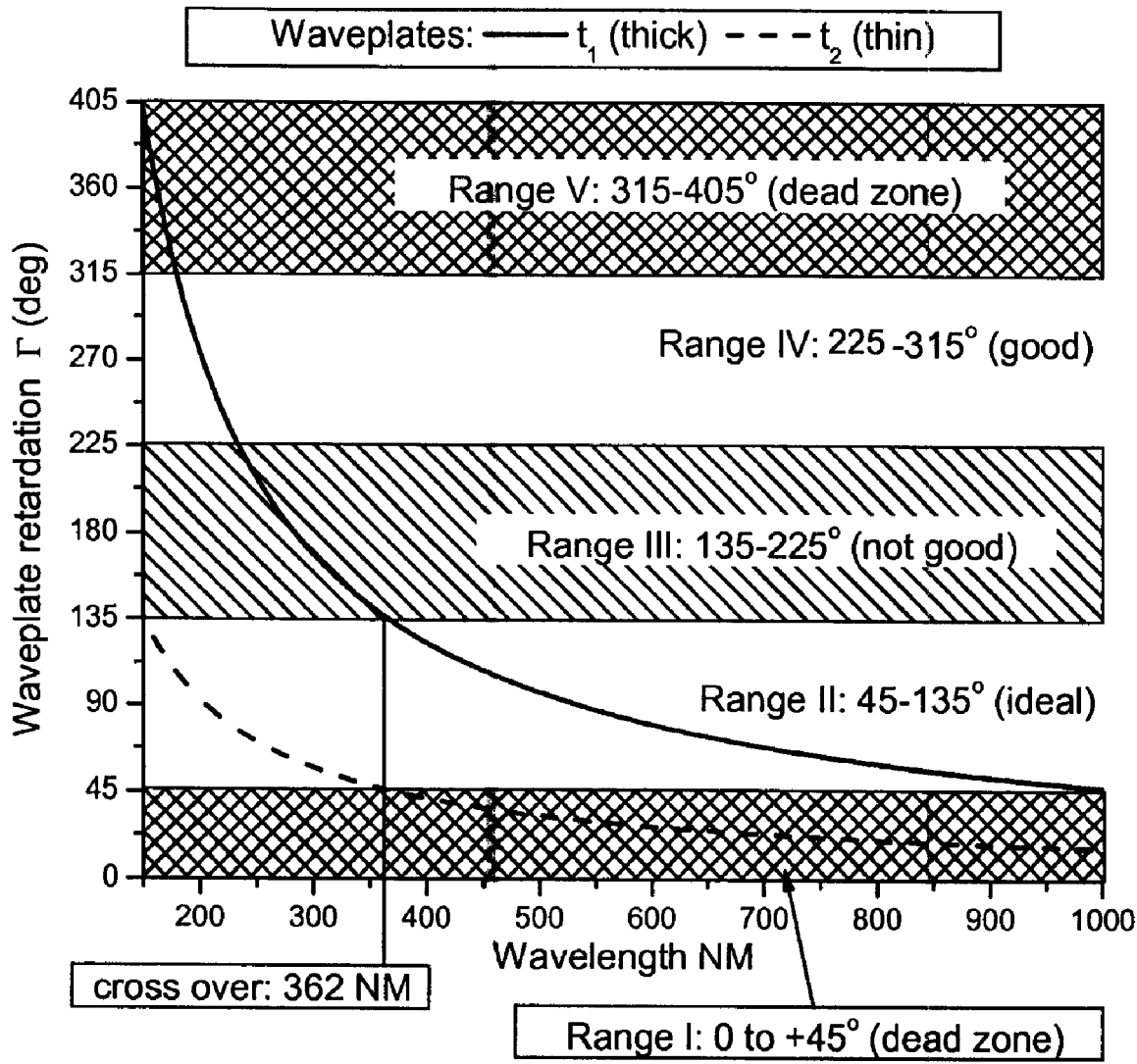
FIG. 5 is a graph illustrating the retardation curves for two waveplates of different thickness from 150 nm to 1000 nm.

The underlying idea may be best illustrated with the help of FIG. 5, which is a graphical representation of retardation versus wavelength for retardation curves of a standard waveplate 1, called "thick" waveplate with thickness $t_1$ and a waveplate 2, called "thin" waveplate with thickness $t_2$. If we assume for this example that useful retardation of either waveplate must be in a range of 90°±45°, i.e., from 45° to 135° for optimal sensitivity to the additional $\sin(\Delta)$ term of an RCE, which depends on the waveplate properties through a multiplicative factor of the sine of the waveplate retardation $\Gamma$, i.e., the available information is proportional to the product $\sin(\Gamma)\sin(\Delta)$, the sensitivity of the system will be 100% at $\Gamma$=90° retardation and it will drop to about 70%

$$\left(\frac{1}{\sqrt{2}}\right)$$

at either extreme, i.e., at $\Gamma=45°$ and $\Gamma=135°$. The 135° crossing for the thick waveplate in FIG. 5 occurs at about 362 nm in this example, where we use $MgF_2$ as the birefringent waveplate material. In order to extend the useful range with the required sensitivity of greater than 70% in this example, the thin waveplate is introduced with a retardation of 45° at the cross-over point. In this manner, there is always retardation available that provides >70% system sensitivity. The relationship for the required thickness ratio of the two waveplates is general and does not depend on the material out of which the plates are constructed or the cross-over wavelength, but is merely a function of the desired minimum sensitivity of the system. For instance, if we allow the minimum sensitivity to occur at 90°±45°, the following relationships for the waveplate retardations $\Gamma$ are true: for waveplate#1 $\Gamma_1=\Delta n\, t_1/\lambda_o=135°$, and for waveplate#2 $\Gamma_2=\Delta n\, t_2/\lambda_o=45°$, where $\Delta n$ is the difference in index of refraction for the birefringent waveplate material and $\lambda_o$ is the cross-over wavelength. By taking the ratio of the expressions above we obtain a thickness ratio of $t_2/t_1=45°/135°=1/3$, or equivalently $$t_2 = \frac{t_1}{3},$$

which is a general expression independent of the cross-over wavelength $\lambda_o$ and also independent of the waveplate material. While the thickness of the first waveplate may be chosen according to its wavelength range of operation and depending on the waveplate material, the thickness of the second waveplate, if constructed out of the same material, is determined entirely by the required minimum sensitivity of the system. In this example the thickness ratio is 1/3, but it can be any ratio depending on the choice of sensitivity.

The diagram of FIG. 5 is divided into five (5) zones labeled Range I to Range V. The retardation zones around 0 and 360°, Range I and V, respectively, are the dead zones for the above example, where the system has lost too much sensitivity in order to return useful information for wavelengths that fall within this range of retardation. Range III is where the retardation is close to 180° and the system turns into an effective rotating polarizer system. This is not a desired condition but it allows the extraction of some information from the data, although it is considered incomplete information. Range II is the ideal range for operation of a rotating compensator ellipsometer since the retardation falls within the range of highest sensitivity between 45° and 135°. This example shows that over the entire available spectrum of wavelengths, the combination of thick and thin waveplate allows operation within Range II and hence the sensitivity of the system is assured throughout the available spectral range. In fact, the wavelength range for which useful retardation is available is extended from 362 nm all the way to 150 nm. Redundant retardation exists in a relatively narrow band (Range IV) from 180-230 nm for which the thick waveplate assumes retardation values around 270°, which is equivalent in sensitivity to Range II. The very fact that a second band of sensitivity is available for a single waveplate rotating compensator ellipsometer is the basis for the before mentioned U.S. Pat. No. 5,973,787, which recognizes that the spectral range of operation may be broadened by allowing operation in both Range II and Range IV with good sensitivity, as well as Range III with limited sensitivity. However, even with the above extension, the overall bandwidth of a single compensator ellipsometer is limited by the fundamental physical laws which dictate the dispersion of birefringent materials. As can be seen from the two curves in FIG. 5, extension of a current single compensator design even to 150 nm would require a significantly thinner waveplate, such as waveplate 2 with thickness $t_2$, which results in loss of sensitivity over a wide wavelength range from about 362 to 1000 nm, where the retardation of the waveplate is too close to zero for acceptable operation. In contrast, the ellipsometer disclosed herein is designed to operate specifically in Range II for all wavelengths, and does not suffer from retardations that fall within Range I, III, or V at all, since the complementary waveplate provides proper sensitivity by operation in Range II for those regions.

From the foregoing it may be seen that spectroscopic ellipsometers according to embodiments of the present invention may utilize different waveplates selected to provide phase retardations within an effective range, e.g., Range II or a combination of Range II and Range IV, for complementary wavelength ranges. As used herein, the wavelength ranges for which the waveplates produce retardations in the effective range are said to be complementary if the corresponding wavelength ranges are at least partly non-overlapping.

The system is not limited to operation with two waveplates. Applying the same argument as above, one could envision operation with three, four, or more waveplates, in principle, always applying the same thickness-relationship between consecutive waveplates. However, while the single rotating compensator produces five (5) frequency components of interest, the dual rotating compensator system may produce 25 (5×5) when both waveplates spin at the same time, and so forth for every additional compensator. The task of calculating the system response, even though straight forward in principle, may become increasingly complex and may no longer be practical for a large number of compensators, unless some of them can be parked in a stationary, neutral state while others are rotating. It is emphasized hereby that adding the second compensator is the next logical and practical step, yet this disclosure is not limiting the design to two waveplates only. Three or more waveplates may-be used if so desired, by repeated application of the same rationale.

The single rotating compensator equivalent configuration with both rotating compensators located next to each other on the same side of a sample 420 depicted in FIG. 4 may be implemented for instance as shown in a Source 400—Polarizer 410—Sample 420—First compensator assembly 430—Second Compensator assembly 440—Analyzer 450—Detector 460 configuration. The light from a broadband source 400 is polarized by a polarizer 410, for instance a $MgF_2$ Rochon prism, and is incident on the sample 420. The compensator assemblies 430, 440 may be defined to include first and second waveplates 432, 442, e.g., quarter waveplates, respectively having thicknesses $t_1$ and $t_2$. Each compensator assembly may further include a mount, rotating stage and motor or other device for imparting rotational motion to the waveplate. After reflection from the sample 420 the beam passes through the first waveplate 432 of thickness $t_1$ and immediately afterward through the second waveplate 442 of thickness $t_2$. The order of the first and second waveplates 432 and 442 is arbitrary. The resulting polarization state of light from the source that passes through the polarizer 410 and both waveplates is projected onto the transmission axis of the analyzer 450, which is a polarizer that, depending on the design, may be operated in reverse. The transmitted intensity is detected by a suitable detector 460, such as a charge-coupled device (CCD) or photo diode array (PDA). For simplicity, not shown are any optic that may be required yet which are standard on already existing designs to collimate the diverging light of the source. Also for simplicity not shown are any optic that may be required yet which are standard on already existing designs to image the source onto the wafer to form a small measurement spot for common small spot applications. Further, not shown for simplicity is the dispersive element that is required yet may be standard on already existing designs to separate the different wavelength constituents of the beam in space after the analyzer, so that the intensity for each wavelength may be detected independent of all other wavelengths. Commonly used dispersive elements are optical gratings or prisms, or a combination of both. The waveplates need to rotate, which is done typically with an electrical motor, and the detector readout must be synchronized to the waveplate azimuth. A novel requirement compared to the single rotating compensator ellipsometer, yet a common requirement for prior art dual rotating compensator ellipsometers is that the rotation rate of the two compensators be different and defined by a specific rotation rate ratio, which is a rational number. Also not shown in FIG. 4 is the required yet standard data processing hardware, such as data acquisition hardware and a computer.

In this embodiment, the compensator assemblies 430 and 440 may be configured to rotate their respective waveplates 432, 442 at rotational speeds designated $\omega_1$ and $\omega_2$ respectively. The rotation speeds may be in a fixed ratio $\omega_1:\omega_2=m:n$, where m and n are integer numbers.

It can be shown that a rotation rate ratio for the two waveplates of 2.5:1 provides separation of all available information from the plates into 25 Fourier coefficients when both waveplates rotate at the same time. The frequency components of interest in that configuration are DC, $1\omega$, $2\omega$, $3\omega$, $4\omega$, $5\omega$, $6\omega$, $7\omega$, $8\omega$, $9\omega$, $10\omega$, $12\omega$, and $14\omega$. Although other ratios of rotation rate are possible, 2.5 is the smallest useful ratio. For instance, if the fast spinning waveplate triggers 32 readouts of the detector during one full rotation, which is every 11.25°, 16 frequency constituents are available from discrete Fourier analysis (harmonic analysis), which is sufficient to cover the necessary 14 harmonics for the example given. The slow waveplate would be read 32×2.5=90 times during a full rotation, or every 4.5°. The initial waveplate configuration repeats every other rotation of the slow waveplate and every time the fast waveplate has completed five (5) full rotations.

Figure 6:
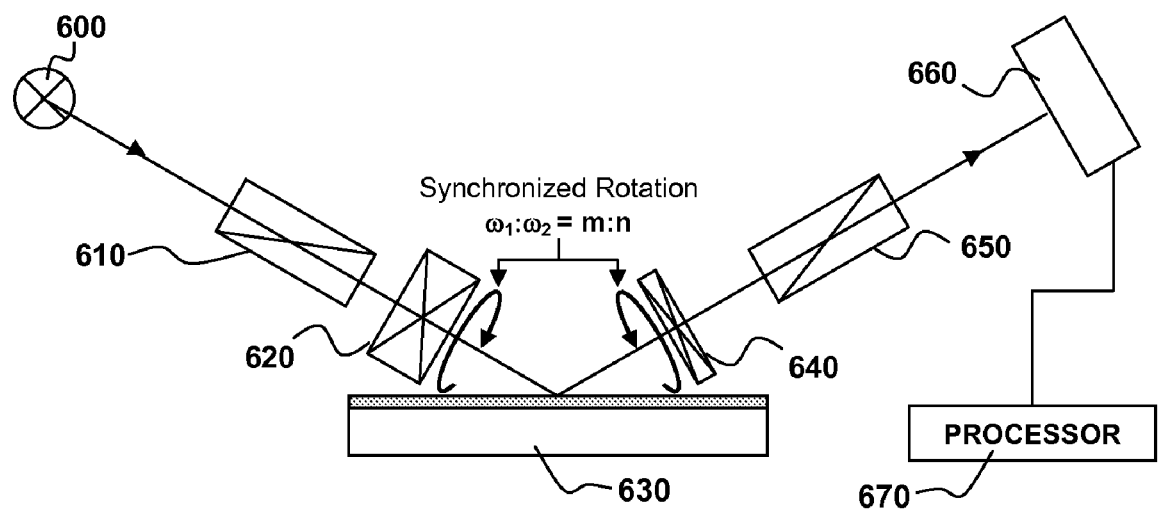
FIG. 6 is a schematic diagram of a complementary dual rotating compensator ellipsometer in a symmetric configuration according to the second embodiment of the present invention.

In a second embodiment of the complementary waveplate dual rotating compensator ellipsometer two compensator assemblies having waveplates of different thickness are located on either side of a sample 630 as illustrated in FIG. 6. In this embodiment two compensators having waveplates of specific and different thickness are mounted on either side of the sample 630 in a so-called symmetric configuration In particular the ellipsometer has a source 600—Polarizer 610—First compensator assembly 620—Sample 630—Second Compensator assembly 640—Analyzer 650—Detector 660 configuration. However, depending on the application, it may be somewhat less ideally suited for the sole purpose of extending the available wavelength range since the incident polarization is being affected by the rotating waveplate, which could make the reflected beam of light more sensitive to additional sample properties, such as the reflection differences of the sample depending on the azimuth of the sample relative to the direction of polarization of the incident beam. In fact, this is a motivation for Mueller matrix spectroscopy with two identical waveplates as in the configuration illustrated in the prior art of FIG. 3. However, this configuration may be equivalent to a single compensator equivalent configuration for samples that feature homogeneous overlayers whose reflection properties do not depend on wafer orientation relative to the direction of polarization. The symmetric configuration may provide, however, unique advantages by combining extension of the wavelength range with potentially available Mueller matrix information in regions of the spectrum where both waveplates happen to have good retardation, for instance that of 180-230 nm in the example of FIG. 5.

In the symmetric configuration two modes of operation are possible. The first mode is identical to that of the single compensator equivalent configuration, with both waveplates spinning at the same time, synchronized, and at a fixed ratio of rotation rate, for instance at the above provided 2.5:1 ratio. This mode of operation is particularly useful when the entire wavelength range can be acquired at the same time, since it provides all of the available information in the shortest amount of time. As used herein "synchronized" rotation of two waveplates means that the two waveplates have a fixed relative angular relation. For instance the angle of one waveplate may be 2.5 times the angle of the other waveplate at all times. Thus, synchronized rotation includes rotation of the two waveplates at different angular speeds with a fixed ratio of the two angular speeds. In some embodiments, the two waveplates may rotate at the same rotational speed. This could be a useful mode of operation for extending the useful range of the apparatus into the infrared.

In a second mode of operation one of the waveplates may spin while the other waveplate is maintained in a neutral position in the beam. Neutrality of a waveplate component may be achieved by aligning its fast or slow axis with the transmission axis of the nearby polarizer or analyzer. For instance the waveplate of the first compensator assembly 620 may be aligned with the polarizer 610 while the waveplate of the second compensator assembly 640 is spinning. Alternatively, the waveplate of the second compensator assembly 640 may be aligned with the analyzer 650 while the waveplate of the first compensator assembly 620 is spinning. The advantages of this mode of operation are that (1) the two waveplates do not need to be synchronized, (2) that fewer Fourier coefficients are generated, which requires fewer readouts of the detector during one full rotation, and (3) the mathematical description simplifies significantly to that of a single rotating compensator system. This mode of operation may be particularly suited for ellipsometers where a full spectrum must be acquired in two steps anyway, for instance because the broadband spectrum is comprised of contributions from two different light sources, such as a Deuterium lamp for the deep UV part of the spectrum and a Xenon lamp for the remaining UV and visible to IR part of the spectrum, and the two sources must be switched into the beam consecutively but cannot be used to acquire data at the same time.

In the first embodiment of the proposed ellipsometer, where both waveplates are on the same side of the sample, the waveplate of the compensator that is closest to the analyzer (or polarizer) may also be parked while in the beam, assuming neutrality when its slow or fast axis is aligned with the corresponding polarizer or analyzer, depending on the configuration, and the same arguments of reduction to an effective single compensator system as described in the previous paragraph apply. In contrast to the symmetric configuration, there is no null-effect parking position for the waveplate on the far-side of either polarizer or analyzer, resulting in a stationary phase shift when it is stopped and remains in the beam while the waveplate next to the analyzer or polarizer is rotating. However, the stopped waveplate does not add any physically significant information to the beam of light and from knowledge of its retardation the additional phase shift can be accounted for during data analysis, so that also in this configuration a simplified mode of operation is possible.

While it is possible to couple a dual rotating compensator with a scanning monochromator to obtain broad spectral information, such a configuration is considered inferior to the present invention because scanning takes time. The scanning monochromator could be positioned before the polarizer to allow only light of one wavelength to enter the system, or it could be placed after the analyzer to select only one wavelength constituent of the transmitted beam for intensity measurement with the detector.

To facilitate operation at the lower end of the wavelength range, e.g., in the deep UV, ellipsometers of the type depicted in FIG. 4 and FIG. 6 may be configured to permit the beam path to be purged with an inert gas, such as nitrogen. Specifically, the optical components of the ellipsometer may be located within a housing that is coupled to an inert gas source. Inert gas may flow from the source to the housing and through a space between the housing and the sample. This purges an optical path along which the broadband beam can pass without detrimental losses in intensity over the available wavelength range.

A processor 670 may process intensity information measured by the detector 660 to determine the polarization state of the reflected light. This may be done by performing a harmonic analysis on the intensity that has been measured with the detector 660 in evenly spaced angular intervals as a function of waveplate azimuth. The relative amplitude and phase of the non-zero Fourier coefficients of the detected intensity provide the information about the phase A and the magnitude of the reflection coefficients that we seek.

While the above is a complete description of the preferred embodiment of the present invention, it is possible to use various alternatives, modifications and equivalents. Therefore, the scope of the present invention should be determined not with reference to the above description but should, instead, be determined with reference to the appended claims, along with their full scope of equivalents. Any feature, whether preferred or not, may be combined with any other feature, whether preferred or not. In the claims that follow, the indefinite article "A", or "An" refers to a quantity of one or more of the item following the article, except where expressly stated otherwise. The appended claims are not to be interpreted as including means-plus-function limitations, unless such a limitation is explicitly recited in a given claim using the phrase "means for."

What is claimed is:

1. A rotating compensator broadband spectroscopic ellipsometer for evaluating a sample comprising:
    a light source configured to generate a polychromatic light beam characterized by a range of useful wavelengths and a known polarization;
    a first compensator assembly disposed along an optical path of the light beam and a second compensator assembly disposed along the optical path of the light beam, wherein one or both of said first and second compensator assemblies includes a waveplate that is rotatable about an axis substantially parallel to a propagation direction of the light beam
    wherein the first compensator assembly is configured to induce at least a first effective phase retardation value of a polarization state of the light beam over a first range of wavelengths, wherein the first effective phase retardation value is within a range of effective retardations
    wherein the second compensator assembly is configured to induce at least a second effective phase retardation value of a polarization state of the light beam over a second range of wavelengths, wherein the second range of wavelengths is complementary to the first range of wavelengths, and wherein the second effective phase retardation value is within the range of effective retardations;
    an analyzer configured to interact with a portion of the light beam that interacts with the sample and with said first and second compensators; and
    a detector optically coupled to the analyzer, wherein the detector is configured to measure an intensity of light after interaction with the analyzer as a function of wavelength and of a rotation angle of each of the first and second compensators about its respective axis.

2. The broadband spectroscopic ellipsometer of claim 1, further comprising one or more additional compensator assemblies disposed along the optical path of the light beam between the light source and the analyzer.

3. The broadband spectroscopic ellipsometer of claim 1, wherein the first and second compensator assemblies are located on the same side of the sample between a polarizer and the analyzer.

4. The broadband spectroscopic ellipsometer of claim 1, wherein the two compensator assemblies are located on different sides of the sample between a polarizer and an analyzer.

5. The broadband spectroscopic ellipsometer of claim 1, wherein the first and second compensator assemblies are configured to rotate first and second waveplates at the same time but not at the same speed.

6. The broadband spectroscopic ellipsometer of claim 5, wherein a rotation rate of the first waveplate is synchronized to a rotation rate of the second waveplate and a ratio of the rotation rates of the first and second waveplates is fixed.

7. The broadband spectroscopic ellipsometer of claim 6 wherein a ratio of the rotation rates is a ratio m:n, where m and n are integers and wherein the ratio m:n is greater than or equal to 2.5:1.

8. The broadband spectroscopic ellipsometer of claim 6 wherein the rotation rate of the first waveplate is equal to the rotation rate of the second waveplate.

9. The broadband spectroscopic ellipsometer of claim 1 wherein a rotation rate of the first compensator assembly is synchronized to a rotation rate of the second compensator assembly.

10. The broadband spectroscopic ellipsometer of claim 1, wherein the first and second compensator assemblies are located on the same side of the sample between a polarizer and the analyzer and wherein the first compensator assembly includes a first waveplate and the second compensator assembly includes a second waveplate, wherein each waveplate is characterized by two optical axes.

11. The broadband spectroscopic ellipsometer of claim 10 wherein one of two optical axes of the first waveplate is configured to align with a polarization axis of the polarizer to null an effect thereof, and wherein the second waveplate is configured to spin.

12. The broadband spectroscopic ellipsometer of claim 10 wherein the first waveplate has an optical thickness along a path of the light beam through the first waveplate that is different from an optical thickness of the second waveplate along an optical path of the light beam through the second waveplate.

13. The broadband spectroscopic ellipsometer of claim 12 wherein the optical thicknesses of the first and second waveplates are configured such that a shortest wavelength of the first range of wavelengths corresponds to a longest wavelength of the second range of wavelengths.

14. The broadband spectroscopic ellipsometer of claim 12 wherein a ratio of the optical thickness of the second waveplate to the optical thickness of the first waveplate, or vice versa, is greater than or equal to 1/3.

15. The broadband spectroscopic ellipsometer of claim 1, wherein the first and second compensator assemblies are located on different sides of the sample between a polarizer and an analyzer, wherein the first and second compensator assemblies respectively include first and second waveplates, wherein one of two optical axes of the second waveplate is configured to align with a polarization axis of the analyzer to null an effect thereof, and wherein the first waveplate is allowed to spin and deliver the signal generated thereby to the analyzer to define the second mode of single-rotating-compensator operation for the ellipsometer.

16. The broadband spectroscopic ellipsometer of claim 1, wherein the first and second compensator assemblies are located on the same side of the sample between a polarizer and an analyzer, wherein the first and second compensator assemblies respectively include first and second waveplates, wherein one of the first and second waveplates that is closest to the polarizer or analyzer is configured not to rotate, while the other of the first and second waveplates rotates.

17. The broadband spectroscopic ellipsometer of claim 16, wherein a fast or slow axis of the waveplate that is configured not to rotate is fixed and aligned with respect to a polarization axis of the polarizer or analyzer.

18. The broadband spectroscopic ellipsometer of claim 1, wherein the first and second compensator assemblies are located on the same side of the sample between a polarizer and an analyzer, wherein the first and second compensator assemblies respectively include first and second waveplates, wherein one of the first and second waveplates that is closest to the polarizer or analyzer is configured to rotate while the other of the first and second waveplates is not spinning.

19. The broadband spectroscopic ellipsometer of claim 18 wherein the one of the first and second waveplates that is not spinning is configured to introduce a known wavelength dependent phase shift between p- and s-polarized photons of the light beam.

20. The broadband spectroscopic ellipsometer of claim 1 wherein the first and second compensators are selected to obtain adequate sensitivity over a range of wavelengths of interest.

21. The broadband spectroscopic ellipsometer of claim 20 wherein the range of wavelengths of interest is between about 150 nanometers and about 1000 nanometers.

22. The broadband spectroscopic ellipsometer of claim 1, further comprising:
a processor configured to determine a polarization state of the light, after the interaction with the analyzer from the intensities measured by the detector.

23. The broadband spectroscopic ellipsometer of claim 1, further comprising:
a polarizer configured to polarize the light beam before the light beam interacts with the sample.

24. The broadband spectroscopic ellipsometer of claim 23, wherein the polarizer and the analyzer are linear polarizers.

25. The broadband spectroscopic ellipsometer of claim 1 wherein the first and second compensator assemblies are configured to optimize a Fourier coefficient of the intensity of light measured by the detector.

26. The broadband spectroscopic ellipsometer of claim 24 wherein the Fourier coefficient is a sine or cosine term that depends on a relative phase shift introduced by a waveplate.

27. The broadband spectroscopic ellipsometer of claim 1 wherein the range of effective retardations is between (45+180N) degrees and (135+180N) degrees, where N is an integer.

28. The broadband spectroscopic ellipsometer of claim 1 wherein the first and second compensators are configured such that a shortest wavelength of the first range of wavelengths corresponds to a longest wavelength of the second range of wavelengths.

29. The broadband spectroscopic ellipsometer of claim 1, further comprising means for purging an optical path of the light beam with an inert gas.

30. A method of analyzing a sample comprising the steps of:
a) generating a beam of light with a useful range of wavelength constituents and known polarization;
b) inducing a phase retardation between two polarization states of the beam of light using first and second compensator assemblies,
wherein the first compensator assembly induces phase retardations within a specified range of retardations over a first portion of the useful range of wavelengths,
wherein the second compensator assembly induces phase retardations within the specified range of retardations over a second portion of the useful range of wavelengths, wherein the second portion is at least partially complementary to the first portion;
c) rotating a waveplate of one or both of the first and second compensator assemblies about an axis substantially parallel to a propagation direction of the beam of light;
d) subjecting the light beam to interaction with an analyzer after interaction with both the first and second compensator assemblies and the sample; and
e) measuring an intensity of useful wavelength constituents of the light beam after interaction with the analyzer as a function of compensator azimuth.

31. The method of claim 30 wherein the first compensator and the second compensator are located next to each other, with each compensator comprising a quarter waveplate at its own and specific quarter-wave retardation wavelength.

32. The method of claim 30 wherein the first compensator assembly includes a first quarter waveplate disposed in the path of the light beam from the polarizer incident to the sample to induce phase retardations of a polarization state of the light beam; and wherein the second compensator assembly includes a second quarter waveplate disposed in the path of a light beam reflected from the sample, wherein the first and second quarter waveplates are configured to induce phase retardations of a polarization state of the light beam.

33. The method of claim 32 wherein c) includes rotating the first and second quarter waveplates at the same time but not at the same speed.

34. The method of claim 33 wherein a ratio of rotation rates of the first and second quarter waveplates is a ratio m:n, where m and n are integers and wherein the ratio m:n is greater than or equal to 2.5:1.

35. The method of claim 33 wherein a rotation rate of the first waveplate is equal to a rotation rate of the second waveplate.

36. The method of claim 32 further comprising separating information from the two waveplates into independent Fourier coefficients.

37. The method of claim 32 wherein c) includes synchronizing an azimuth of the first waveplate to an azimuth of the second waveplate.

38. The method of claim 30 wherein the first and second compensator assemblies respectively comprise first and second quarter waveplates, and wherein c) includes aligning one of two optical axes of the first quarter waveplate with the analyzer to null an effect thereof, and allowing the second waveplate to spin in a single rotating compensator mode.

39. The method of claim 30 wherein the first and second compensator assemblies respectively comprise first and second waveplates wherein c) includes maintaining one of the first and second waveplates in a neutral position while rotating the other of the first and second waveplates.

40. The method of claim 30 wherein the first and second compensator assemblies are selected to achieve sufficient sensitivity over the useful range of wavelengths.

41. The method of claim 40 wherein the useful range of wavelengths is from 150 nm to 1000 nm.

42. The method of claim 30, further comprising determining a polarization state of the light after d) and e).

43. The method of claim 30 wherein a) includes generating a beam of polychromatic light from a light source; and polarizing the light beam before the light beam interacts with the sample.

44. The method of claim 42, wherein polarizing the light beam includes linearly polarizing the light beam.

45. The method of claim 30 wherein the specified range of retardations is between (45+180N) degrees and (135+180N) degrees, where N is an integer.

46. The method of claim 30 wherein the first and second compensators are configured such that a lowest wavelength of the first range of wavelengths corresponds to a highest wavelength of the second range of wavelengths.

47. The method of claim 30, further comprising purging an optical path of the light beam with an inert gas.

48. The method of claim 30 wherein c) includes rotating the first and second compensators synchronously at a pre-determined ratio of rotation rate.

49. An apparatus for evaluating a sample comprising: means for generating a beam of polychromatic light having a range of wavelengths and a known polarization for interacting with the sample; a first compensating means for inducing phase retardations of a polarization state of the light beam over a first range of wavelengths, wherein the first compensating means and the first range of wavelengths are selected such that at least a first effective phase retardation value induced over the first range of wavelengths lies within a range of effective phase retardations; a second compensating means for inducing phase retardations of a polarization state of the light beam over a second range of wavelengths, wherein the second range of wavelengths is out side of and complementary to the first range of wavelengths, wherein the second range of wavelengths and the second compensating means are selected such that at least a second effective phase retardation value induced over the second range of wavelengths lies within the range of effective phase retardations; each of said first and second compensating means being rotatable about an axis substantially parallel to the propagation direction of the light beam; an analyzing means for interacting with the light beam after the light beam interacts with the sample and with said first and second compensating means; and detecting means for measuring the intensity of the light after the interaction with the analyzing means as a function of wavelength and of a rotation angle of each of the first and second compensating means about its respective axis, including light intensities of those wavelengths corresponding to said first and second wavelength ranges.

50. The apparatus of claim 49 wherein the first and second compensators are configured to rotate synchronously.

* * * * *